(12) United States Patent
Noordhoek et al.

(10) Patent No.: US 8,774,484 B2
(45) Date of Patent: Jul. 8, 2014

(54) X-RAY APPARATUS

(75) Inventors: Nicolaas Jan Noordhoek, Eindhoven (NL); Angelique Balguid, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 183 days.

(21) Appl. No.: 13/386,680

(22) PCT Filed: Sep. 1, 2010

(86) PCT No.: PCT/IB2010/053926
§ 371 (c)(1),
(2), (4) Date: Jan. 24, 2012

(87) PCT Pub. No.: WO2011/030257
PCT Pub. Date: Mar. 17, 2011

(65) Prior Publication Data
US 2012/0155738 A1 Jun. 21, 2012

(30) Foreign Application Priority Data
Sep. 8, 2009 (EP) .................................... 09169694

(51) Int. Cl.
*G06K 9/00* (2006.01)

(52) U.S. Cl.
USPC ........................................ 382/132

(58) Field of Classification Search
USPC .................... 382/128–132; 600/428
See application file for complete search history.

(56) References Cited

U.S. PATENT DOCUMENTS

| 7,532,704 | B2 | 5/2009 | Hempel | |
| 2007/0244393 | A1* | 10/2007 | Oshiki et al. | 600/463 |
| 2008/0013675 | A1* | 1/2008 | Boese et al. | 378/14 |
| 2009/0041179 | A1* | 2/2009 | Zellerhoff | 378/4 |

FOREIGN PATENT DOCUMENTS

| DE | 102006030811 A1 | 1/2008 |
| EP | 0917856 A1 | 5/1999 |
| WO | 2007130433 A2 | 11/2007 |

* cited by examiner

*Primary Examiner* — Amara Abdi

(57) ABSTRACT

An X-ray apparatus 10 executes a first scan of an object during a forward movement F and a second scan during a backward movement B. Due to the wiper-like movement of the X-ray imaging device 18 supported by an arm 12 of the X-ray apparatus 10, the time between two scans may be very short.

15 Claims, 3 Drawing Sheets

X-RAY APPARATUS

FIELD OF THE INVENTION

The invention relates to the field of X-ray imaging, in particular to the field of computer tomography. Specifically, the invention relates to an X-ray apparatus, a method of controlling an X-ray apparatus, a computer-readable medium and a program element.

BACKGROUND OF THE INVENTION

Computed tomography (CT) is a medical imaging method in which an X-ray apparatus scans an object of interest, for example a patient, and takes a series of X-ray images. From the series of X-ray images, a three-dimensional image of the inside of the object may be generated with the aid of digital geometry processing methods. As a rule, the series of pictures is taken during the movement of an X-ray imaging device about an axis of rotation. The volume data encoding the three-dimensional image of the object of interest may further be manipulated, for example it may be processed to be displayed as slices of the object of interest on a display device. Generally, various structures inside the object of interest may be visualized based on the ability of the structures to block an X-ray beam from the X-ray imaging device.

CT is a very useful tool in supporting the diagnosis of cancer. In particular, for the diagnosis of a hepatocellular carcinoma (HCC) in a first phase of the procedure a contrast agent may be injected into the liver of a patient and after a waiting period the liver is scanned for the first time. In a second phase of the procedure, again a contrast agent is injected into the liver and after a second waiting period that is longer than the waiting period before the first scan, the liver is scanned a second time. By comparing the two scans, a physician may be supported in the diagnosis of a hepatocellular carcinoma. In the scan of the first phase both a HCC and pseudo lesions (like arterioportal shunts) are visualized due to the contrast agent. In the scan of the second phase, a HCC generally shows ring-like enhancements, which is not expected for pseudo lesions, allowing to distinguish HCC a from other structures and lesions of the liver. The ring-like structure shows up in the images, since HCC is a type of tumour that comprises small vessels surrounding the tumour which are filled by the contrast agent dispersing inside the liver after a certain time corresponding to the second waiting period after the second contrast agent injection.

The time period after which the contrast agent reaches the small vessels may be short. Therefore, a conventional computer tomography apparatus may not be able to execute two scans of the patient while the contrast agent is dispersing inside the liver up to the small vessels. This is the reason why, conventionally, the contrast agent is injected two times during the diagnosis.

However, injecting two times a contrast agent may be a great stress for the patient. Further, the whole procedure may become very time-consuming.

SUMMARY OF THE INVENTION

There may be a need to enable an acquisition of three-dimensional images by scanning a patient at least two times during a short time period.

This need may be met by the subject-matter of the independent claims. Exemplary embodiments of the invention are evident from the dependent claims.

A first aspect of the invention relates to an X-ray apparatus. According to an embodiment of the invention, the X-ray apparatus comprises an X-ray imaging device, an arm for supporting the X-ray imaging device and a controller for controlling the X-ray imaging device and the arm. The controller is adapted to control a first movement of the arm, such that the X-ray imaging device is moving along a first path in a forward direction around an object. The X-ray imaging device is adapted to take a first plurality of images of the object during the first movement. The controller is adapted to generate first volume data from the first plurality of images. The controller is adapted to control a second movement of the arm, such that the X-ray imaging device is moving along a second path in a backward direction. The X-ray imaging device is adapted to take a second plurality of images of the object during the second movement. The controller is adapted to generate a second volume data from the second plurality of images.

In other words, the X-ray apparatus may execute a first scan of an object during a forward movement and a second scan during a backward movement. If the two scans were executed in the same direction, a movement of the X-ray imaging device into an initial position would be necessary between the two scans. Due to the wiper-like movement of the X-ray imaging device, this movement may be omitted and time may be saved.

An X-ray imaging device may comprise a source of X-rays, for example an X-ray tube, and an X-ray detector. The X-ray imaging device may take an image of the object, for example a patient, by transmitting a beam of X-rays from the X-ray source through the object onto the detector.

The first and second plurality of images may be a series of images that are taken at a series of time points, which may be equidistant, e.g. during a rotational movement of the X-ray imaging device in one direction. As a rule, the first plurality of images contains the same number of images as the second plurality of images.

The arm for supporting the X-ray imaging device may be an elongated member that may partially surround the object. In particular, there may be a region of the object that is not surrounded by the arm. The X-ray source of the X-ray imaging device may be attached to one end of the arm and the X-ray detector of the X-ray imaging device may be attached to the other end of the arm. Further, there may be an actuator, for example a motor, that may be controlled by the controller to move the arm.

The controller of the X-ray apparatus may comprise a computer with in- and output devices that are connected to sensors, like the X-ray detector or an obstacle detection mechanism, and actuators, like the motor for moving the arm.

It has to be understood, that the forward direction and the backward direction may be mere opposite directions. For example, it would be possible that the X-ray imaging apparatus is executing or conducting the first movement in the backward direction and the second movement in the forward direction. Further, the forward and the backward direction need not to be exactly anti-parallel. For example, the first path and the second path need not be equivalent. It may be possible that there is a small angle, for example smaller than 10°, between the first path and the second path. Further, it may be possible that the second path comprises or is at least a part of the second path. However, the first path and the second path may coincide.

According to an embodiment of the invention, the X-ray apparatus is a tomography apparatus. In other words, the X-ray apparatus may be adapted to generate the first and second volume data in such a way that views of slices through the object may be generated.

According to an embodiment of the invention, the first movement is a rotational movement and the second movement is a rotational movement. For example, the arm supporting the X-ray source and the X-ray detector may be moved in such a way around the object that the X-ray source and the X-ray detector are performing rotational or pivoting movements around a common axis of rotation.

According to an embodiment of the invention, the arm is a C-arm. For example, the elongated member comprised by the C-arm may be formed as a section of a circle.

According to an embodiment of the invention, the arm is solely movable in a region not completely surrounding the object. For example, the motor moving the arm may be attached to the arm in such a way, that the arm may be moved by the motor from one end to the other end. Since the arm may not completely surround the object and the devices attached to the end of the arms (the X-ray source and the X-ray detector) may be arranged opposite to each other with respect to the object, there may be a region, which may not be reached by the ends of the arm.

According to an embodiment of the invention, the controller is adapted to start the second movement at a predefinable time after a start of the first movement. A user of the X-ray apparatus, for example a physician, may input a time value into the controller to adjust the start of the second movement with respect to the first movement. The time value may be suitably selected for a specific diagnosis to be supported by the acquired images.

According to an embodiment of the invention, the controller is adapted to start the second movement less than 30 seconds after a start of the first movement.

By adjusting the time between the two starts of the two movements or the time between the end of the first movement and the start of the second movement, the scans may be timely adjusted in such a way, that e.g. the ring-like structure appearing in a HCC examination in the second scan may be displayed or recognized in the best way.

A time period of less than 30 seconds may be needed to scan the patient two times after the injection of a contrast agent, to support the diagnosis of a cancer of the HCC type. Only an X-ray apparatus that is adapted to scan the patient two times in less than 30 seconds may be adapted to support the diagnosis of this type of cancer with only one injection of contrast agent. With a conventional X-ray C-arm apparatus, scans may only be made in one direction, making it possibly too slow to return to the rotation start position and make a second scan within 30 seconds.

According to an embodiment of the invention, the controller is adapted to wait for a predefinable time period between the first movement and the second movement. A user of the X-ray apparatus may not only input or adjust the times between the starts of the movements but also the time between the end of the first movement and the start of the second movement.

According to an embodiment of the invention, the controller is adapted to start the second movement directly after the first movement. There may be no waiting period between the two movements.

According to an embodiment of the invention, the controller is adapted to control the movement of the arm in a safety movement before the first movement, wherein the controller is adapted to detect if an obstacle is blocking the path during the safety movement. For safety reasons, the X-ray apparatus may have to check, whether the whole movement of the arm may be conducted without an obstacle in the way of the arm. For example, it may be possible that the physician treating the patient has not left the region around the patient, which may be occupied during the movement of the arm.

According to an embodiment of the invention, the controller is adapted to control a movement of the arm in at least three movements, such that the X-ray imaging device is moving alternating in forward and backward directions, wherein the X-ray imaging device is adapted to take a plurality of images during each of the at least three movements. For example, it may be possible that the X-ray imaging device is scanning the patient in a forward, a backward and a forward direction. In such a way, three scans of the patient or the object may be done with only short time periods between the scans.

According to an embodiment of the invention, the controller is adapted to control the movement of the arm in at least three movements such that each successive movement is directly started after a preceding movement. The X-ray apparatus may have the capability to start the second (third, fourth . . . ) scan (or movement) directly after the next scan. The user may decide how many scans he wants and/or what the delay or waiting times between the scans are. The waiting times between the scans may be different. The time between the starts of two scans may only be limited by the duration of a single scan and no other overhead.

According to an embodiment of the invention, the X-ray apparatus comprises further a display device, wherein the display device is adapted to display the first volume data as a first display image and the second volume data as a second display image, wherein the display device is adapted to display the images simultaneously. For example, the first and second display images may be displayed side by side on the display device, so that the user of the X-ray apparatus, for example a physician, easily may compare the two display images. Additionally or alternatively, it is possible, that the first and the second display images are overlaid or merged with each other. The two display images may display views of slices through the object.

According to an embodiment of the invention, the X-ray apparatus is adapted to take the first and second plurality of images before generating the first and second volume data. For example, the X-ray apparatus may comprise a memory that is large enough to store more than one series of images. Therefore, the speed of the scan may not be slowed down by the processing of the taken images.

A further aspect of the invention relates to a method of controlling an X-ray apparatus.

According to an embodiment of the invention, the method comprises the steps of: moving an arm of the X-ray apparatus in a first movement, such that an X-ray imaging device supported by the arm is moving along a first path in a forward direction around an object; taking a first plurality of images of the object with the X-ray imaging device during the first movement; generating a first volume data from the first plurality of images; moving the arm in a second movement, such that the X-ray imaging device is moving along a second path in a backward direction around the object; taking a second plurality of images of the object with the X-ray imaging device during the second movement; generating second volume data from the second plurality of images.

In other words, during two consecutive forward and backward movements two scans of the object may be taken. The object may be scanned during the first movement and after an optional waiting period, the second movement with a second scan may be executed by the X-ray apparatus.

According to an embodiment of the invention, the method further comprises the steps of: starting the first movement after an injection of a contrast agent into a region of interest of the object; starting the second movement while the contrast agent is dispersing in the region of interest.

Before the method is conducted, a contrast agent may be injected into the region of interest, for example the liver of a patient. It may be possible, that the first movement starts, while the injection of the contrast agent is not finished, i.e. the steps of moving the arm in a first movement and the injection of a contrast agent may overlap. However, the piercing of the patient, and in particular the liver of the patient, is done before the first movement, and, for example, the injection of the contrast agent may be done by a pump which may be controlled by the controller of the X-ray apparatus. In this way, it may be possible, to synchronize the timing between the start of the injection, the end of the injection, the start of the first movement and/or the start of the second movement.

During the diagnosis of liver cancer, contrast agent may be injected interarterial. After that, the contrast agent will follow the blood stream through the artery and the following blood vessels and will disperse within the region containing the blood vessels. As a rule, a contrast agent injected into an artery of a liver will enter the small blood vessels surrounding a cancer of the HCC type after about 25 to 30 seconds.

The first movement may be a first phase and the second movement may be a second phase of the method. Therefore, the method may be a dual-phase method. The method may be used during treatment or diagnosis of liver cancer. The treatment may be a transarterial chemoembolization (TACE) or an ablation. The dual-phase technique may allow the visualization of hepatocellular carcinoma in two consecutive phases after interarterial contrast injection. These consecutive scans may help to confirm that the lesion is indeed HCC and needs treatment. With this technique, a hepatic arterial injection may be followed by one scan (i.e. in the first phase), a waiting period (typically 25 to 30 seconds) and then a second scan (i.e. second phase). In the first phase, both HCC and pseudo lesions (like arterioportal shunts) may be demonstrated or may show up as hyperattenuating lesions, which may not be distinguished with the scan of the first phase. In the second phase, a HCC should show a ring-like enhancement which is not expected for pseudo lesions, allowing a distinction between the two. A display device, for example a monitor, may parallel demonstrate the same slice level side by side and may give a good overview for assessment.

The dual-phase method may be done in an angio room with only one contrast injection. Pseudo lesions can be distinguished from HCC, which may not always be clear from diagnostic MR or CT, specifically for multi-focal lesions.

In the case, that the X-ray apparatus conducts more than two, for example at least three movements, the method may be a multi-phase method.

Movement during the scans may be described as a wiper motion of the C-arm. The viper movement may imply, that both in a forward rotation of the C-arm a 3D reconstruction can be made, and in backward rotation.

It has to be understood that the method steps described in the context of the X-ray apparatus in the above and in the following may be included in embodiments of the method and vice versa.

A further aspect of the invention is a computer-readable medium, in which a computer program for controlling an X-ray apparatus is stored, which when being executed by a processor is adapted to carry out the steps of the method as described in the above and in the following.

A computer-readable medium may be a floppy disk, a hard disk, a CD, a DVD, an USB (Universal Serial Bus) storage device, a RAM (Random Access Memory), a ROM (Read Only memory) and an EPROM (Erasable Programmable Read Only Memory). A computer readable medium may also be a data communication network, e.g. the Internet, which allows downloading a program code.

A further aspect of the invention relates to a program element for controlling an X-ray apparatus, which, when being executed by a processor, is adapted to carry out the steps of the method described in the above and in the following.

For example, the controller of the X-ray apparatus may comprise a memory and a processor. The memory may store the program element and the processor may be adapted to execute the program element stored in the memory. For example, the program element may be loaded from a computer-readable medium into the memory of the controller.

These and other aspects of the invention will be apparent from and elucidated with reference to the embodiments described hereinafter.

BRIEF DESCRIPTION OF THE DRAWINGS

Below, embodiments of the present invention are described in more detail with reference to the attached drawings.

The reference numerals used in the drawings, and their meanings, are listed in summary form in the list of reference numerals. In principle, identical parts are provided with the same reference numerals in the figures.

DETAILED DESCRIPTION OF EMBODIMENTS

Figure 1:
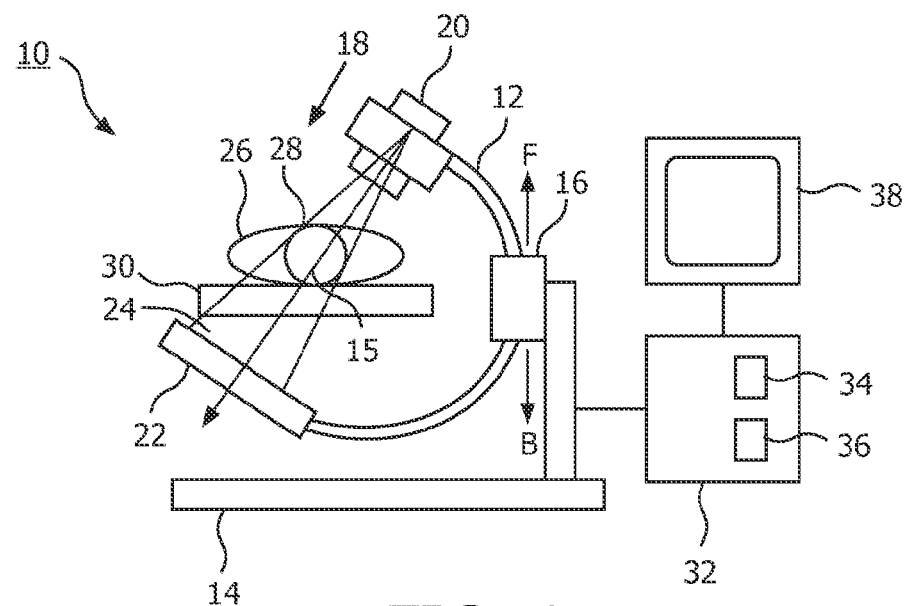
FIG. 1 shows a schematic diagram of an X-ray apparatus according to an exemplary embodiment of the invention.

FIG. 1 shows a schematic diagram of an X-ray apparatus 10. The X-ray apparatus 10 has a C-arm 12 which is attached to a base 14 of the X-ray apparatus 10. The C-arm 12 may be rotated around an axis of rotation 15 with the aid of a motor 16. An X-ray imaging device 18 is attached to the C-arm 12. The X-ray imaging device 18 comprises an X-ray tube 20 attached to one end of the C-arm 12 and an X-ray detector 22 attached to the other end of the C-arm 12. Due to structural limitations of the C-arm device (for example high voltage cables), the movement of the C-arm 12 may be limited to a range of about 200°.

If the X-ray apparatus takes an image, the X-ray tube 20 emits an X-ray beam 24 through a region of interest 28 of a patient 26. The patient 26 lies on a table 30, such that the axis of rotation 15 intersects the region of interest 28. The X-ray beam 24 is more or less blocked by the different structures of the region of interest 28 and falls on the X-ray detector 22.

The X-ray apparatus 10 comprises further a controller 32 for controlling the motor 16, the X-ray tube 20 and the X-ray detector 22. The controller 32 is adapted to control the movement of the C-arm 12 in a forward direction F and in a backward direction B. Further the controller 32 is adapted to activate and deactivate the X-ray tube and to receive and process the sensor data, i.e. the images, of the X-ray detector 22.

The controller 32 comprises a memory 34 and a processor 36. The processor 36 may be adapted to execute the control and calculation functions of the controller 32. In the memory 34, the images taken by the X-ray imaging device 18, at least two series of images taken during two scans, may be stored. Further in the memory 34, at least two sets of volume data generated from at least two series of images may be stored.

The controller 32 may be further adapted to generate or calculate display images from the volume data stored in the memory 34, such that the display images may be displayed on a monitor 38. For example, the display images may be views of slices through the region of interest 28 of the patient 26.

Figure 2:
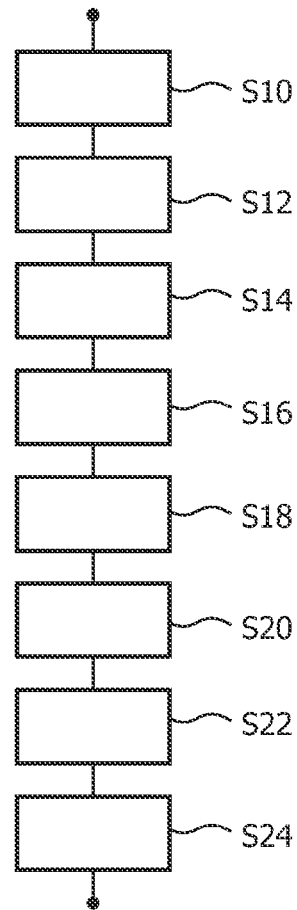
FIG. 2 shows a flow diagram of a method according to an exemplary embodiment of the invention.

FIG. 2 shows a flow diagram for a method that may be executed by a physician and the X-ray apparatus 10 shown in FIG. 1.

In a step S10, the physician pierces a hollow needle into the patient 26, in particular into an artery of the liver of the patient 26 inside the region of interest 28.

In a step S12, the X-ray apparatus 10 is activated and the apparatus 10 may execute a safety movement. With the safety movement, the X-ray imaging device 18 is moved around the patient 26 like in the following (first and second) movements. However, in the safety movement the patient 28 is not scanned. An obstacle detection device that may be attached to the C-arm 12 detects, whether an obstacle is in the way of the C-arm 12 and the imaging device 18. For example, it may be possible, that the physician that has pierced the hollow needle into the patient has not left the region, in which the C-arm 12 is moving.

In a step S14, the injection of a contrast agent through the hollow needle is started. The step S14 may be conducted before, during or after the safety movement of step S12. Further, the starting of the injection may be executed by the X-ray apparatus 10, in particular the controller 32, which may be adapted to actuate a pump that pumps the contrast agent into the artery of the patient. In one case, the physician only pierces the needle and activates the X-ray apparatus 10. After that all steps are automatically conducted by the X-ray apparatus 10.

In a step S16, the X-ray imaging device 18 is moved around the axis of rotation 15 in a first movement in the forward direction F. During the first movement, the X-ray imaging device 18 takes a first plurality or first series of pictures that are stored in the memory 34 of the controller 32.

After the first movement, in step S18, the X-ray imaging device is moved around the patient 26 in a second movement in the backward direction B. During the second movement, the X-ray imaging device 18 takes a second plurality or second series of images that are stored in the memory 34 of the controller 32.

In an optional step S20, further alternating movements in the forward and backward direction may be conducted by the X-ray apparatus 10. During each of the movement a further series or plurality of images may be taken and stored.

In a step S22, the controller 32, in particular the processor 36 of the controller 32, creates first volume data from the first plurality of images and second volume data from the second plurality of images. Also, further volume data may be created from the further plurality of images. It is possible, that the generation or creation of volume data is conducted directly after taking each plurality of images or that first all the pluralities of images are taken and after that all the volume data is generated.

In a step S24, the controller 32 generates display images from the first and second volume data and displays these images on the monitor 38. For example, the two display images are displayed side by side on the monitor 38 or are displayed alternating in consecutive time periods or are overlaid in one image.

Figure 3:
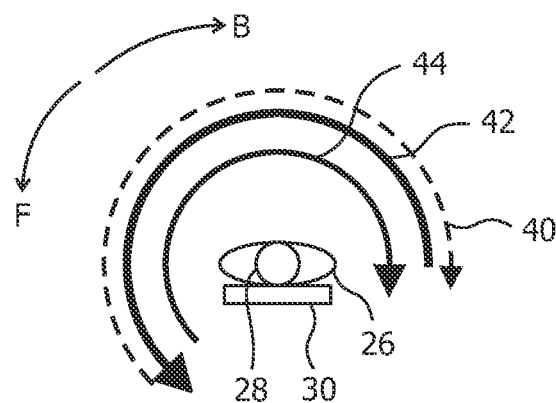
FIG. 3 schematically shows the movement of the X-ray imaging device according to an exemplary embodiment of the invention.

FIG. 3 shows a possible movement of the X-ray imaging device 18 during the method shown in FIG. 2.

In an optional safety movement 40, the C-arm 12 is rotated around the patient 26. Following the safety movement 40, a first movement 42 is done in a forwarding direction F following the same path as in the safety movement 40. After the first movement 42, a second movement 44 in the backward direction B is done following the same path as during the first movement 42.

Figure 4:
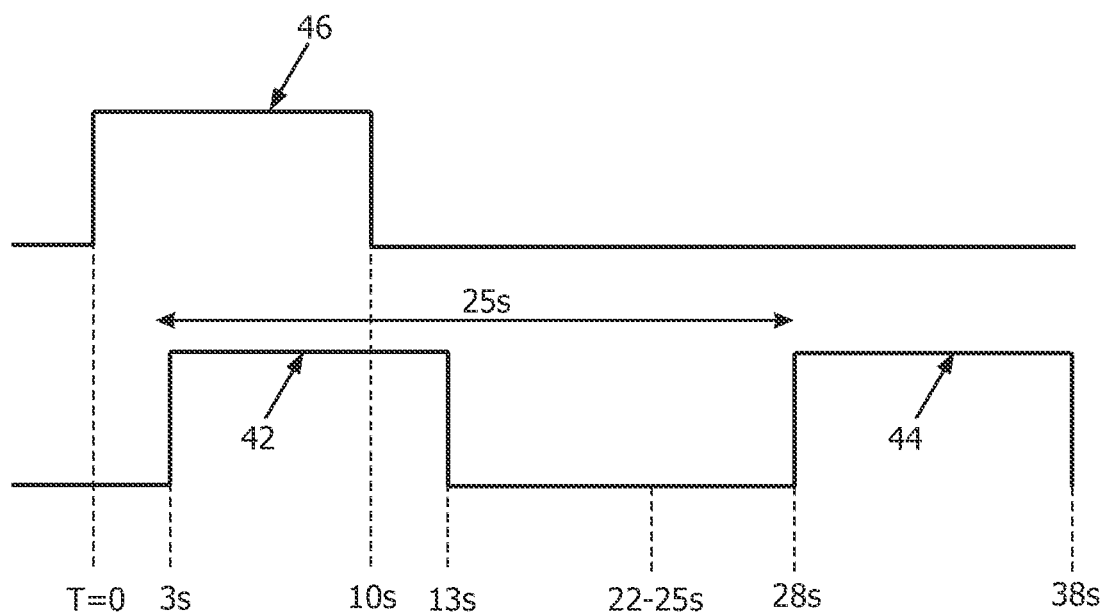
FIG. 4 shows time relations of an embodiment of a method according to an exemplary embodiment of the invention.

FIG. 4 shows aspects of time relations of the different method steps of the method of FIG. 2. At a time T=0, the injection of the contrast agent 46 is started. Before, the hollow needle may have been pierced into the patient by the physician. At a time T=3 s, the first movement 42 is started. During the following 10 s, a plurality of images is taken by the X-ray imaging device 18 up to T=13 s, where the first movement ends. Also, in the meantime at T=10 s, the injection of the contrast agent 46 has been finished. During the time between 3 s and 10 s, the injection of the contrast agent 46 and the first movement 42 are overlapping. For example, the contrast agent may be injected with a rate of 2 ml/s, i.e. altogether 20 ml are injected.

In the time between T=13 s and T=22-25 s, the patient may be allowed to breathe again, since in this time, the X-ray apparatus 10 does not scan the patient 26. Between T=28 s and T=38 s, the second movement 44 is conducted and the X-ray apparatus 10 is taking a second plurality of images during this time. The second movement 44 is starting 25 s after the start of the first movement 42.

Many of the parameters shown in FIG. 4 may be adjusted by the user of the X-ray apparatus, for example the physician, by inputting different values. With tuning these parameters, the diagnosis of HCC cancer may be optimized. For example, the physician may adjust the rate of the contrast injection, the duration of the contrast injection, the time between the start of the contrast injection and the start of the first scan, the time between the start of the first scan and the second scan and alternatively, the time between the end of the first scan 42 and the start of the first second scan 44.

Figure 5:
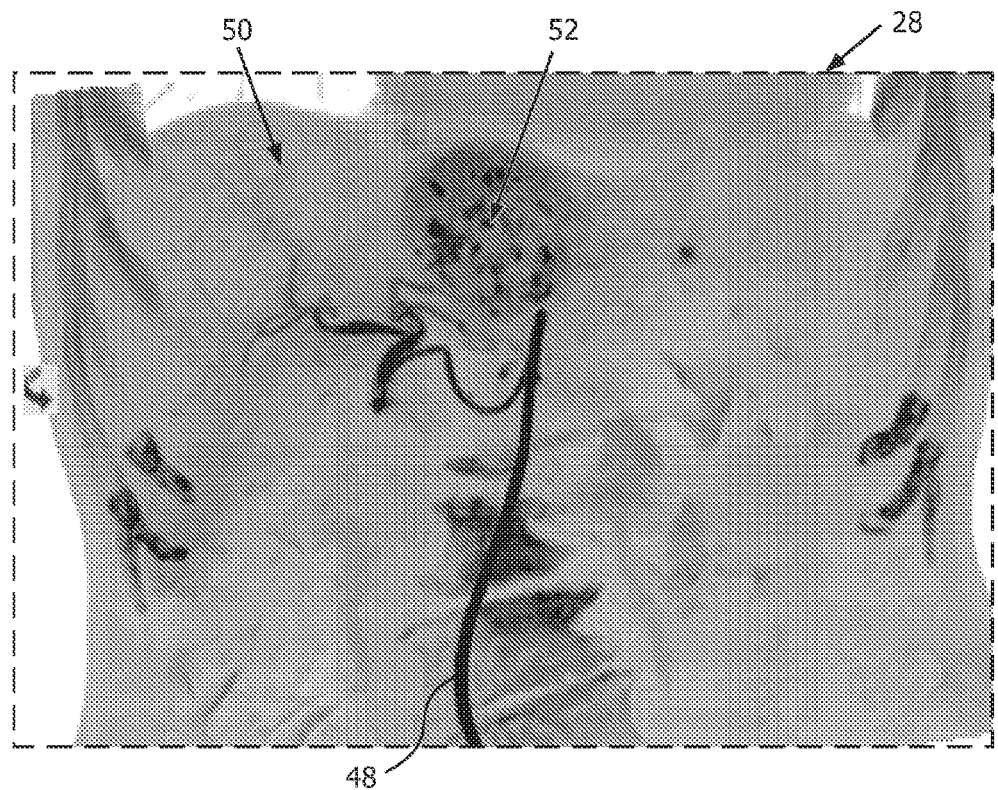
FIG. 5 is a picture of a slice through a patient taken during the first movement of the X-ray apparatus according to an exemplary embodiment of the invention.

FIG. 5 shows a slice through the patient 26 taken during the first movement 42. As can be seen from FIG. 5, a contrast agent 48 has been injected which is dispersing inside the liver 50 of the patient 26. Due to the injection of the contrast agent, a tumour 52, which may be a cancer tumour 52 shows up in the picture of FIG. 5.

Figure 6:
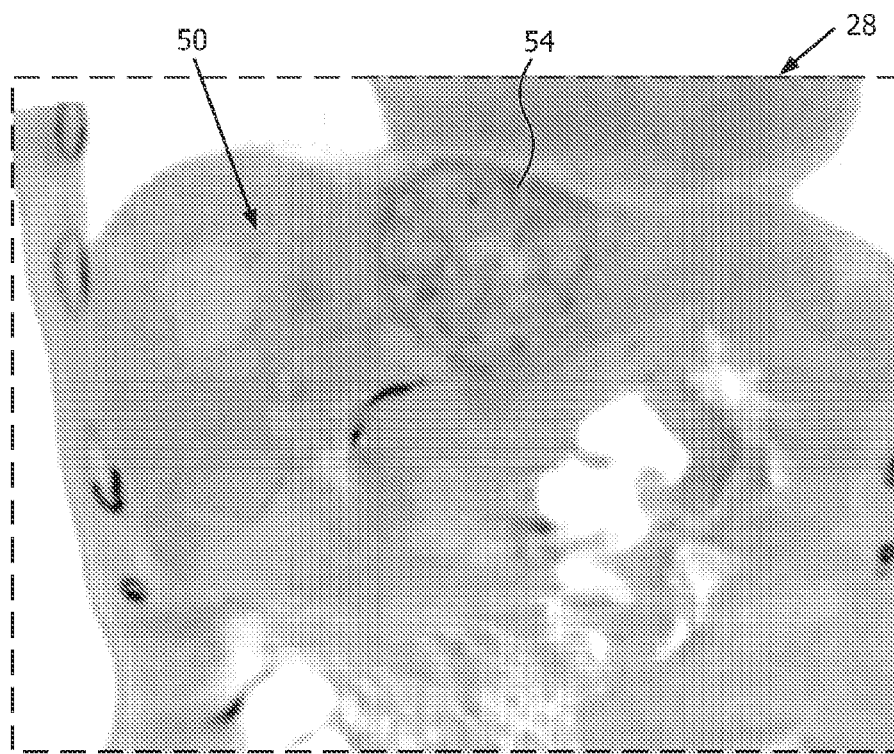
FIG. 6 is a picture of the slice through the patient taken during the second movement of the X-ray apparatus according to an exemplary embodiment of the invention.

FIG. 6 is a picture analog to FIG. 5, taken during the second movement 44. A contrast agent 48 has further dispersed inside the liver 50 of the patient and now a ring-like structure 44 indicates, that the cancer or tumour 52 may be a HCC.

The functional modules may be implemented as programmed software modules or procedures, respectively; however, one skilled in the art will understand that the functional modules may be implemented fully or partially in hardware.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practising the claimed invention, from a study of the drawings, the disclosure, and the appended claims. In the claims, the word "comprising" does not exclude other elements or steps, and the indefinite article "a" or "an" does not exclude a plurality. A single processor or controller or other unit may fulfil the functions of several items recited in the claims. The mere fact that certain measures are recited in mutually different dependent claims does not indicate that a combination of these measures cannot be used to advantage. Any reference signs in the claims should not be construed as limiting the scope.

LIST OF REFERENCE NUMERALS

10 X-ray apparatus
12 C-arm
14 base
15 axis of rotation
16 motor
18 X-ray imaging device
20 X-ray tube
22 X-ray detector
24 X-ray beam
26 patient
28 region of interest
30 table
32 controller
34 memory
36 processor
38 monitor
40 safety movement
42 first movement
44 second movement
46 injection of contrast agent
48 contrast agent
50 liver
52 cancer
54 ring like-structure

The invention claimed is:

1. An X-ray apparatus, comprising:
an X-ray imaging device;
an arm for supporting the X-ray imaging device; and
a controller for controlling a single injection of a contrast agent into an object, the X-ray imaging device and the arm,
wherein the controller is adapted to control in a first phase a first movement of the arm while the single injection of the contrast agent is not finished, such that (i) the X-ray imaging device is moving along a first path in a forward direction (F) around the object, and (ii) a timing of the first movement and the single injection of the contrast agent overlap,
wherein the X-ray imaging device is adapted to take a first plurality of images of the object during the first movement,
wherein the controller is adapted to generate first volume data from the first plurality of images in which both hepatocellular carcinoma (HCC) and pseudo lesions show up as hyperattenuating lesions that may not be distinguished from one another;
wherein the controller is adapted to control in a second phase a second movement of the arm, such that the X-ray imaging device is moving along a second path in a backward direction (B),
wherein the X-ray imaging device is adapted to take a second plurality of images of the object during the second movement, and
wherein the controller is adapted to generate second volume data from the second plurality of images in which HCC shows up as a ring-like enhancement which is not expected for pseudo lesions, allowing a distinction between the two with only one contrast agent injection.

2. The X-ray apparatus of claim 1, wherein the first movement is a rotational movement and the second movement is a rotational movement.

3. The X-ray apparatus of claim 1, wherein the arm is a C-arm.

4. The X-ray apparatus of claim 1, wherein the arm is solely movable in a region not completely surrounding the object.

5. The X-ray apparatus of claim 1, wherein the controller is adapted to start the second movement at a predefinable time after a start of the first movement.

6. The X-ray apparatus of claim 1, wherein the controller is adapted to start the second movement less than 30 s after a start of the first movement.

7. The X-ray apparatus of claim 1, wherein the controller is adapted to wait for a predefinable time period between the first movement and the second movement.

8. The X-ray apparatus of claim 1, wherein the controller is adapted to control a movement of the arm in a safety movement before the first movement, and wherein the controller is adapted to detect if an obstacle is blocking the path during the safety movement.

9. The X-ray apparatus of claim 1, wherein the controller is adapted to control a movement of the arm in at least three movements, such that the X-ray imaging device is moving in alternating forward and backward directions, and wherein the X-ray imaging device is adapted to take a plurality of images during each of the at least three movements.

10. The X-ray apparatus of claim 1, further comprising:
a display device,
wherein the display device is adapted to display the first volume data as a first display image and the second volume data as a second display image, and
wherein the display device is adapted to display the images simultaneously.

11. The X-ray apparatus of claim 1, wherein the X-ray apparatus is adapted to take the first and second plurality of images before generating the first and second volume data.

12. A method of controlling an X-ray apparatus, the method comprising the steps of:
moving an arm of the X-ray apparatus in a first phase in a first movement while controlling a single injection of a contrast agent into an object is not finished, such that (i) an X-ray imaging device supported by the arm is moving along a first path in a forward direction (F) around the object and (ii) a timing of the first movement and the single injection of the contrast agent overlap;
taking a first plurality of images of the object with the X-ray imaging device during the first movement;
generating first volume data from the first plurality of images in which both hepatocellular carcinoma (HCC) and pseudo lesions show up as hyperattenuating lesions that may not be distinguished from one another;
moving the arm in a second phase in a second movement, such that the X-ray imaging device is moving along a second path in a backward direction (B) around the object;
taking a second plurality of images of the object with the X-ray imaging device during the second movement; and
generating second volume data from the second plurality of images in which HCC shows up as a ring-like enhancement which is not expected for pseudo lesions, allowing a distinction between the two with only one contrast agent injection.

13. The method of claim 12, further comprising the steps of:
   starting the first movement after starting the single injection of the contrast agent into a region of interest of the object; and
   starting the second movement while the contrast agent is dispersed in the region of interest.

14. A non-transitory computer-readable medium embodied with a computer program executable by a processor for controlling an X-ray apparatus to carry out the steps of the method of claim 12.

15. A non-transitory program element embodied with a computer program executable by a processor for controlling an X-ray apparatus to carry out the steps of the method of claim 12.

* * * * *